(12) United States Patent
Peddy et al.

(10) Patent No.: US 9,981,947 B2
(45) Date of Patent: May 29, 2018

(54) POLYMORPHIC FORMS OF NILOTINIB HYDROCHLORIDE

(71) Applicant: DR. REDDY'S LABORATORIES LIMITED, Hyderabad (IN)

(72) Inventors: Vishweshwar Peddy, Hyderabad (IN); Ramanaiah Chennuru, Nellore (IN); Srividya Ramakrishnan, Hyderabad (IN)

(73) Assignee: DR. REDDY'S LABORATORIES LIMITED, Hyderabad (IN)

( * ) Notice: Subject to any disclaimer, the term of this patent is extended or adjusted under 35 U.S.C. 154(b) by 0 days. days.

(21) Appl. No.: 15/402,890

(22) Filed: Jan. 10, 2017

(65) Prior Publication Data

US 2017/0260162 A1    Sep. 14, 2017

Related U.S. Application Data

(62) Division of application No. 14/786,902, filed as application No. PCT/IB2014/060935 on Apr. 23, 2014, now Pat. No. 9,580,408.

(30) Foreign Application Priority Data

Apr. 24, 2013 (IN) ............... 1795/CHE/2013

(51) Int. Cl.
    *C07D 401/14* (2006.01)
(52) U.S. Cl.
    CPC ................. *C07D 401/14* (2013.01)
(58) Field of Classification Search
    CPC ................................................... C07D 401/14
    See application file for complete search history.

(56) References Cited

U.S. PATENT DOCUMENTS

| | | | |
|---|---|---|---|
| 8,163,904 B2 | 4/2012 | Manley et al. | |
| 8,227,477 B2 | 7/2012 | Sterimbaum et al. | |
| 8,343,984 B2 | 1/2013 | Manley et al. | |
| 8,592,442 B2 | 11/2013 | Sterimbaum et al. | |
| 8,703,788 B2 | 4/2014 | Reddy et al. | |
| 9,580,408 B2 | 2/2017 | Peddy et al. | |
| 2013/0158059 A1 | 6/2013 | Piran et al. | |
| 2013/0210847 A1 | 8/2013 | Kompella et al. | |

FOREIGN PATENT DOCUMENTS

| | | |
|---|---|---|
| WO | 2011086541 A1 | 7/2011 |
| WO | 2012055351 A1 | 5/2012 |

OTHER PUBLICATIONS

IP.com Journal, "NLT HCl Crystalline Forms", May 26, 2009, No. IPCOM000183524D, pp. 1 to 11, vol. 9(12B)—issue No. 14.
IP.com Journal, "Crystalline Forms of NLT HCl", Mar. 8, 2010, No. IPCOM000193749D, pp. 1 to 3, vol. 10(3B)—issue No. 11.
IP.com Journal, "Crystalline forms of 4-methyl-N-[3-(4-methyl-1H-imidazol-1-yl)-5-(trifluoromethyl)phenyl]-3-[[4-(3-pyridinyl)-2-pyrimidinyl]amino]-benzamide salts", Nov. 18, 2010, No. IPCOM000201702D, pp. 1 to 8, vol. 10(12A)—issue No. 18.
IP.com Journal, "Crystalline Form of 4-methyl-N-[3-(4-methyl-1H-imidazol-1-yl)-5-(trifluoromethyl)phenyl]-3-[[4-(3-pyridinyl)-2-pyrimidinyl]amino]-benzamide", Apr. 29, 2010, No. IPCOM000195326D, pp. 1 and 2, vol. 10(5A)—issue No. 25.
IP.com Journal, "Amorphous 4-methyl-N-[3-(4-methyl-1H-imidazol-1-yl)-5-(trifluoromethyl)phenyl]-3-[[4-(3-pyridinyl)-2-pyrimidinyl]amino]-benzamide salts", Jul. 1, 2010, No. 000197295, pp. 1 to 9, vol. 10(7B)—issue No. 3.
International Search Report for corresponding International Patent Application No. PCT/IB2014/060935, dated Dec. 31, 2014.
International Preliminary Report on Patentability for corresponding International Application No. PCT/IB2014/060935, dated Oct. 27, 2015.
Written Opinion for corresponding International Patent Application No. PCT/IB2014/060935, dated Dec. 31, 2014.
International Search Report for corresponding International Patent Application No. PCT/IB2015/056015, dated Dec. 30, 2015.
Written Opinion for corresponding International Patent Application No. PCT/IB2015/056015, dated Dec. 30, 2015.

*Primary Examiner* — Golam M Shameem
(74) *Attorney, Agent, or Firm* — Pergament & Cepeda LLP; Milagros A. Cepeda; Edward D. Pergament

(57) ABSTRACT

Crystalline Forms R5, R5a, R5b and R6 of nilotinib hydrochloride and processes for their preparation.

9 Claims, 5 Drawing Sheets

POLYMORPHIC FORMS OF NILOTINIB HYDROCHLORIDE

This application is a Divisional of U.S. patent application Ser. No. 14/786,902, filed Oct. 23, 2015, which is a National Stage Application under 35 U.S.C. § 371 of PCT International Application No. PCT/IB2014/060935, filed Apr. 23, 2014, which claims the benefit of Indian Provisional Application No. 1795/CHE/2013, filed Apr. 24, 2013, all of which are hereby incorporated by reference in their entireties.

INTRODUCTION

The present application provides crystalline forms of nilotinib hydrochloride designated as Form R5, Form R5a, Form R5b, Form R6 and processes for their preparation thereof.

BACKGROUND OF THE INVENTION

The drug compound having the adopted name "nilotinib hydrochloride" has a chemical name 4-methyl-N-[3-(4-methyl-1H-imidazol-1-yl)-5-(trifluoromethyl)phenyl]-3-[[4-(3-pyridinyl)-2-pyrimidinyl]amino]-benzamide monohydrochloride, and is structurally represented by Formula I.

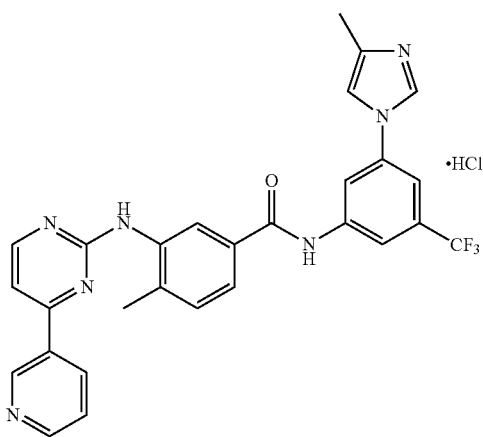

Formula I

Nilotinib hydrochloride is a kinase inhibitor, approved as nilotinib hydrochloride monohydrate, sold using the tradename Tasigna®, in the form of capsule for the treatment of chronic phase and accelerated phase Philadelphia chromosome positive chronic myelogenous leukemia (CML) in adult patients resistant to or intolerant to prior therapy that included imatinib.

International application publication No. WO2007/015871 A1 describes salts of 4-methyl-N-[3-(4-methyl-1H-imidazol-1-yl)-5-(trifluoromethyl)phenyl]-3-[[4-(3-pyridinyl)-2-pyrimidinyl]amino]-benzamide, wherein the salt is a hydrochloride salt, hydrochloride monohydrate, monophosphate salt, diphosphate salt, sulfate salt, methanesulfate salt, ethanesulfonate salt, benzene sulfonate salt, p-toluene sulfonate salt, citrate salt, fumarate salt, malonate salt, malate salt, tartrate salt, etc., their polymorphic forms and process for the preparation thereof. Further, it also discloses the crystalline forms of nilotinib hydrochloride designated as Form A and Form B, process for their preparation and process for the preparation of nilotinib hydrochloride monohydrate.

International application publication No. WO2007/015870 A2 describes substantially pure crystalline forms of nilotinib hydrochloride designated as Form A, Form A', Form A", Form B, Form B', Form $S_B$, Form $S_B'$, Form C, Form C', Form $S_C$, Form D, Form $S_E$, mixture of Form B and Form D, and amorphous form of Nilotinib hydrochloride. Further, it also discloses substantially pure crystalline forms A and B of Nilotinib free base and substantially pure crystalline forms A and B of Nilotinib sulfate salt.

International application publication No. WO2010/054056 A2 describes polymorphic forms of nilotinib hydrochloride designated as forms T1, T2, T3, T4, T5, T6, T7, T8, T9, T10, T11, T12, T13, T14, T15 T16, T17, T18, and T19. Further, it also describes solid dispersion of nilotinib hydrochloride in combination with a pharmaceutically suitable excipient.

International application publication No. WO2011/163222 describes polymorphic forms of nilotinib hydrochloride designated as forms T20, T27, T28 and T29.

International application publication No. WO2011/086541 A1 describes a crystalline form of nilotinib hydrochloride monohydrate having an X-ray diffraction pattern comprising peaks at 5.70, 7.56, 9.82, 15.01, 17.31 and 27.68±0.2 degrees 2-theta and process for its preparation.

International application publication No. WO2012/055351 A1 describes a crystalline form of nilotinib hydrochloride monohydrate having an X-ray diffraction pattern comprising peaks at 4.987, 8.430, 11.309, 14.403, 17.219, 19.225 and 25.544 degrees 2-theta and process for its preparation.

International application publication No. WO2012/070062 A2 describes nilotinib hydrochloride crystalline form H1, characterized by peaks in the powder x-ray diffraction spectrum having 2-theta angle positions at about 8.6, 11.4, 13.2, 14.3, 15.5, 17.3, 19.2 and 25.3±0.2 degrees and process for its preparation.

US application publication No. 2013/0210847 A1 describes nilotinib hydrochloride dihydrate, characterized by peaks in the powder X-ray diffraction pattern at 4.3, 8.7, 9.5, 11.3, 13.2, 14.4, 17.3, 18.6, 19.3, 20.8, 22.2 and 25.3 degrees 2-theta (±0.1 degrees 2-theta).

IP.com Journal (2010), 10(36), 11 describes the crystalline forms T24, T25, and T26 of nilotinib hydrochloride and process for their preparation.

IP com Journal (2010), 10(12A), 18 describes the crystalline forms of nilotinib hydrochloride designated as Forms T19 and T20 and process for their preparation.

IP.com Journal (2009), 9(12B), 14 describes the nilotinib hydrochloride crystalline forms T2-T6, T9 and T11-T13 and process for their preparation.

IP.com Journal (2010), 10(5A), 25 describes the nilotinib hydrochloride crystalline form T5 and process for its preparation.

IP.com Journal (2010), 10(7B), 3 describes a method for the preparation of the 4-methyl-N-[3-(4-methyl-1H-imidazol-1-yl)-5-(trifluoromethyl)phenyl]-3-[[4-(3-pyridinyl)-2-pyrimidinyl]amino]benzamide salts in amorphous form.

The discovery of new polymorphic forms and/or solvates of a drug or a pharmaceutically useful compound provide opportunity to improve the characteristics of a pharmaceutically acceptable dosage form of the drug with a targeted release profile or other desired characteristics.

Despite the aforementioned disclosures mentioning various polymorphic forms, there is a need for new polymorphic forms of nilotinib hydrochloride and processes for their preparation.

SUMMARY OF THE INVENTION

The present application provides crystalline forms of nilotinib hydrochloride designated as Form R5, Form R5a, Form R5b, Form R6 and processes for their preparation thereof.

In an embodiment, the present application provides crystalline nilotinib hydrochloride, designated as Form R5, characterized by data selected from the group consisting of: an x-ray powder diffraction pattern with peaks at about 6.27±0.2, 15.44±0.2, 16.15±0.2, 24.07±0.2 and 26.11±0.2 degrees 2-theta; an x-ray powder diffraction pattern with peaks at about 11.26±0.2, 12.24±0.2, 12.54±0.20, 18.81±0.2 and 27.94±0.2 degrees 2-theta; an x-ray powder diffraction pattern substantially as depicted in FIG. 1; and combination thereof.

In another embodiment, the present application encompasses a process for preparing nilotinib hydrochloride Form R5 comprising the steps of:
a) obtaining a solution of nilotinib hydrochloride in acetic acid;
b) adding a hydrocarbon solvent and/or an ether solvent to the solution of step a);
c) maintaining at a temperature of about 0° C. to about 50° C.; and
d) isolating nilotinib hydrochloride Form R5.

In another embodiment, the present application encompasses a process for preparing nilotinib hydrochloride Form R5 comprising the steps of:
a) obtaining a suspension of nilotinib hydrochloride in acetic acid;
b) maintaining the suspension of step a) at a temperature of about 0° C. to about 50° C.; and
c) isolating nilotinib hydrochloride Form R5.

In an embodiment, the present application encompasses a process for preparing nilotinib hydrochloride Form R5 comprising the steps of:
a) obtaining slurry of nilotinib hydrochloride in acetic acid and ether solvent.
b) maintaining the slurry of step a) at a temperature of about 0° C. to about 50° C.;
c) isolating nilotinib hydrochloride form R5.

In an embodiment, the present application provides crystalline nilotinib hydrochloride, designated as Form R5a, characterized by data selected from the group consisting of: an x-ray powder diffraction pattern with peaks at about 6.29±0.2, 7.31±0.2, 15.45±0.2, 16.18±0.2, 24.10±0.2 and 26.15±0.2 degrees 2-theta; an x-ray powder diffraction pattern substantially as depicted in FIG. 2; and combinations thereof. Nilotinib hydrochloride Form R5a may be further characterized by an x-ray powder diffraction pattern having additional peaks at about 11.26±0.2, 12.25±0.2, 12.55±0.2, 18.86±0.2, 27.98±0.2 degrees 2-theta.

In another embodiment, the present application encompasses a process for preparing nilotinib hydrochloride Form R5a comprising, drying the crystalline nilotinib hydrochloride Form R5 at a temperature less than about 45° C.

In the present application provides crystalline nilotinib hydrochloride, designated as Form R5b, characterized by data selected from the group consisting of: an x-ray powder diffraction pattern with peaks at about 6.28±0.2, 7.29±0.2, 7.56±0.2, 15.54±0.2, 16.07±0.2 and 21.91±0.2 degrees 2-theta; an x-ray powder diffraction pattern substantially as depicted in FIG. 3; and combinations thereof. Nilotinib hydrochloride Form R5b may be further characterized by an x-ray powder diffraction pattern having additional peaks at about 11.72±0.2, 12.45±0.2, 29.49±0.2 degrees 2-theta.

In another embodiment, the present application encompasses a process for preparing nilotinib hydrochloride Form R5b comprising, drying the crystalline nilotinib hydrochloride Form R5 or Form R5a at a temperature of about 60° C. to about 80° C.

In an embodiment, the present application provides crystalline nilotinib hydrochloride, designated as Form R6, characterized by data selected from the group consisting of: an x-ray powder diffraction pattern with peaks at about 7.56±0.2, 10.16±0.2, 12.42±0.2, 20.32±0.2 and 27.97±0.2 degrees 2-theta; an x-ray powder diffraction pattern with peaks at about 8.93±0.2, 11.76±0.2, 15.53±0.2, 17.71±0.2, 19.57±0.2, 21.72±0.2 and 23.40±0.2 degrees 2-theta; an x-ray powder diffraction pattern substantially as depicted in FIG. 4; an x-ray powder diffraction pattern substantially as depicted in FIG. 5; and combinations thereof.

In another embodiment, the present application encompasses a process for preparing nilotinib hydrochloride Form R6 comprising the steps of:
a) obtaining a solution of nilotinib hydrochloride in acetic acid;
b) adding a hydrocarbon solvent and/or an ether solvent to the solution of step a);
c) maintaining the reaction mixture of step b) at a temperature of about 0° C. to about 50° C.;
d) isolating the obtained crystalline compound; and
e) drying at a temperature of about 100° C. to about 120° C. to obtain nilotinib hydrochloride Form R6.

In another embodiment, the present application encompasses a process for preparing nilotinib hydrochloride Form R6 comprising, drying the crystalline nilotinib hydrochloride Form R5 or Form R5a or Form R5b at a temperature of about 100° C. to about 120° C.

In an embodiment, the present application encompasses a process for preparing nilotinib hydrochloride Form R6 comprising the steps of:
a) obtaining a suspension of nilotinib hydrochloride in acetic acid;
b) maintaining the suspension of step a) at a temperature of about 0° C. to about 50° C.; and
c) isolating the obtained crystalline compound; and
d) drying at a temperature of about 100° C. to about 120° C. to obtain nilotinib hydrochloride Form R6.

In an embodiment, the present application encompasses a process for preparing nilotinib hydrochloride Form R6 comprising the steps of:
a) obtaining slurry of nilotinib hydrochloride in acetic acid and ether solvent.
b) maintaining the slurry of step a) at a temperature of about 0° C. to about 50° C.;
c) isolating the obtained crystalline compound; and
d) drying at a temperature of about 100° C. to about 120° C. to obtain nilotinib hydrochloride Form R6.

In an embodiment, the present application provides pharmaceutical composition comprising crystalline forms of nilotinib hydrochloride designated as Form R5, Form R5a, Form R5b or Form R6 and at least one pharmaceutically acceptable excipient.

BRIEF DESCRIPTION OF THE DRAWINGS

FIG. 2 illustrative a characteristic X-ray powder diffraction pattern of nilotinib hydrochloride Form R5a.

DETAILED DESCRIPTION

The present application provides crystalline forms of nilotinib hydrochloride designated as Form R5, Form R5a, Form R5b, Form R6 and processes for the preparation thereof.

Figure 1:
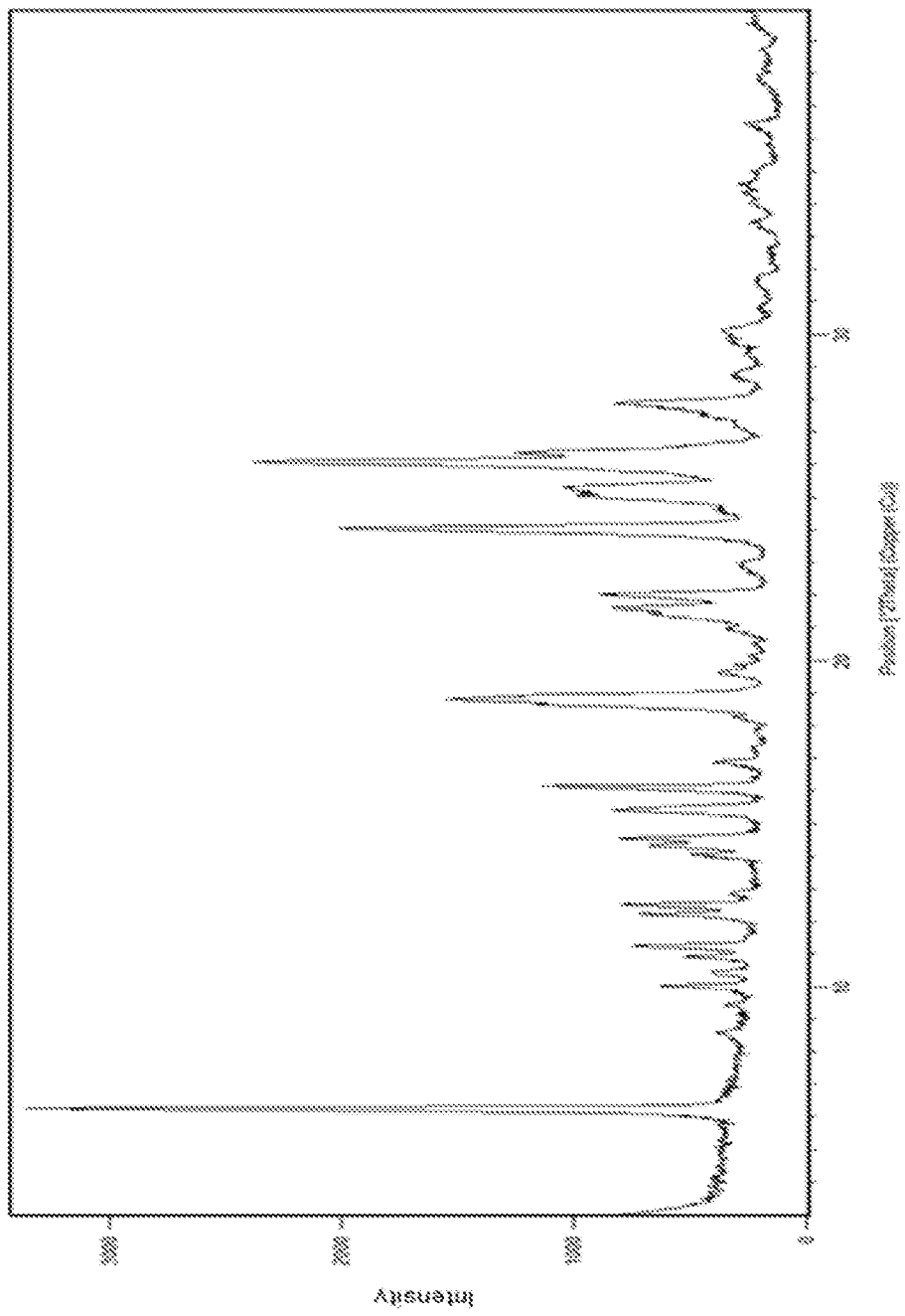
FIG. 1 illustrative a characteristic X-ray powder diffraction pattern of nilotinib hydrochloride Form R5.

In an embodiment, the present application provides crystalline nilotinib hydrochloride, designated as Form R5, characterized by data selected from the group consisting of: an x-ray powder diffraction pattern with peaks at about 6.27±0.2, 15.44±0.2, 16.15±0.2, 24.07±0.2 and 26.11±0.2 degrees 2-theta; an x-ray powder diffraction pattern with peaks at about 11.26±0.2, 12.24±0.2, 12.54±0.20, 18.81±0.2 and 27.94±0.2 degrees 2-theta; an x-ray powder diffraction pattern substantially as depicted in FIG. 1; and combination thereof.

In another embodiment, the present application encompasses a process for preparing nilotinib hydrochloride Form R5 comprising the steps of:
a) obtaining a solution of nilotinib hydrochloride in acetic acid;
b) adding a hydrocarbon solvent and/or an ether solvent to the solution of step a);
c) maintaining at a temperature of about 0° C. to about 50° C.; and
d) isolating nilotinib hydrochloride Form R5.

Step a) involves obtaining a solution of nilotinib hydrochloride in acetic acid.

Obtaining a solution according to step a) includes dissolving nilotinib hydrochloride in acetic acid or obtaining a solution of nilotinib hydrochloride in acetic acid as a final step in the preparation of the compound. Nilotinib hydrochloride may be obtained by the process known in the art. The solution of step a) may be provided at any temperature ranging from about 0° C. to about reflux temperature of the solvent, preferably at about 10° C. to about 80° C., more preferably at about 20° C. to about 50° C., most preferably at about 25° C. to about 35° C.

The solution may optionally be treated with activated charcoal and then filtered to remove the carbon. The solution may optionally be filtered by passing through paper, glass fiber, or other membrane material, or a bed of a clarifying agent such as Celite. Depending upon the equipment used, as well as the concentration and temperature of the solution, the filtration apparatus may need to be heated or cooled to avoid undesired crystallization.

Step b) involves adding a hydrocarbon solvent and/or an ether solvent to the solution of step a).

The hydrocarbon solvent that may be used in step b) is selected from n-pentane, n-heptane, n-hexane or the like. In a preferred embodiment, n-heptane is used. The ether solvent that may be used in step b) is selected from petroleum ether, diisopropyl ether, methyl tert-butyl ether or the like. In a preferred embodiment methyl tert-butyl ether is used.

In an embodiment, a hydrocarbon solvent and an ether solvent may be added to the solution of step a) in a sequential manner. For example, hydrocarbon solvent followed by an ether solvent or an ether solvent followed by a hydrocarbon solvent is added to the solution of step a).

In an embodiment, mixture of a hydrocarbon solvent and an ether solvent may be added to the solution of step a).

The hydrocarbon solvent and/or an ether solvent or mixtures thereof may be added to the solution obtained in step a) at a temperature of about 0° C. to about 50° C. Preferably at about 10° C. to about 40° C., more preferably at about 25° C. to about 35° C.

In a preferred embodiment, a hydrocarbon solvent followed by an ether solvent is added to the solution of step a) at a temperature of about 25° C. to about 35° C.

Optionally, seed crystals of Form R5 or R5a may be added to the reaction mixture of step b). The seed crystals of crystalline Form R5 may be obtained according to the process disclosed in the present application. The seed crystals of Form R5 may be added prior to the addition of a hydrocarbon or an ether solvent or after to the addition of a hydrocarbon or an ether solvent and before to step c). The seeding may be done at a temperature of about 0° C. to about 50° C. Preferably the seeding is done at a temperature of at about 25° C. to about 35° C. In an embodiment, the reaction mixture of step b) is obtained after the seeding step.

Step c) involves maintaining the reaction mixture of step b) at a temperature of about 0° C. to about 50° C.

The reaction mixture of step b) is maintained at a temperature of about of about 0° C. to about 50° C. for sufficient time. Sufficient time as disclosed herein is the time required to ensure the formation of crystalline nilotinib hydrochloride. In an embodiment, the reaction mixture is maintained for a time period of about 30 minutes to about 72 hours.

In an embodiment, the reaction mixture is maintained at a temperature of about 10° C. to about 40° C., more preferably at about 25° C. to about 35° C.

Step d) involves isolating nilotinib hydrochloride Form R5. The crystalline nilotinib hydrochloride Form R5 is isolated in a manner known per se, and depending on the solvent used, which include, but not limited to filtration by gravity or by suction/vacuum, distillation, centrifugation, or slow evaporation or the like. In an embodiment, nilotinib hydrochloride Form R5 may be isolated by filtration under vacuum and suction drying at a temperature of about 25° C. to about 35° C.

In another embodiment, the present application encompasses a process for preparing nilotinib hydrochloride Form R5 comprising the steps of:
a) obtaining a suspension of nilotinib hydrochloride in acetic acid;
b) maintaining the suspension of step a) at a temperature of about 0° C. to about 50° C.; and
c) isolating nilotinib hydrochloride Form R5.

Step a) involves obtaining a suspension of nilotinib hydrochloride in acetic acid.

The nilotinib hydrochloride suspension according to step a) may be obtained by combining nilotinib hydrochloride with acetic acid at temperature of about 0° C. to about 50° C., preferably at about 10° C. to about 40° C., more preferably at about 25° C. to about 35° C. The amount acetic acid used for obtaining a suspension ranges from about 1 ml to about 5 ml per 1 g of nilotinib hydrochloride, based on the temperature range selected.

Step b) involves maintaining the suspension of step a) at a temperature of about 0° C. to about 50° C.

The suspension of step a) may be maintained at a temperature of about 0° C. to about 50° C. In an embodiment, the suspension of step a) is maintained at a temperature of about 10° C. to about 40° C., more preferably at about 25°

C. to about 35° C. The suspension is maintained for a sufficient time to ensure the conversion of nilotinib hydrochloride to crystalline nilotinib hydrochloride Form R5.

In an embodiment, the suspension is maintained for a time period of about 30 minutes to about 72 hours.

Step c) involves isolating the nilotinib hydrochloride Form R5. The crystalline nilotinib hydrochloride is isolated in a manner known per se, and depending on the solvent used, which include, but not limited to filtration by gravity or by suction/vacuum, distillation, centrifugation, or slow evaporation or the like. In an embodiment, nilotinib hydrochloride Form R5 may be isolated by filtration under vacuum and suction drying at a temperature of about 25° C. to about 35° C.

In an embodiment, the present application encompasses a process for preparing nilotinib hydrochloride Form R5 comprising the steps of:
a) obtaining slurry of nilotinib hydrochloride in acetic acid and ether solvent.
b) maintaining the slurry of step a) at a temperature of about 0° C. to about 50° C.;
c) isolating nilotinib hydrochloride form R5.

Obtaining slurry according to step a) includes taking acetic acid and ether and adding nilotinib hydrochloride or dissolving nilotinib hydrochloride in acetic acid and adding ether. Nilotinib hydrochloride may be obtained by the process known in the art. The reaction mixture of step a) may be provided at any temperature ranging from about 0° C. to about reflux temperature of the solvent, preferably at about 10° C. to about 80° C., more preferably at about 20° C. to about 50° C., most preferably at about 25° C. to about 35° C.

The ether solvent that may be used in step a) is selected from petroleum ether, diisopropyl ether, methyl tert-butyl ether or the like. In a preferred embodiment methyl tert-butyl ether is used.

Optionally, seed crystals of Form R5 or R5a may be added to the reaction mixture of step a). The seed crystals of crystalline Form R5 may be obtained according to the process disclosed in the present application. The seeding may be done at a temperature of about 0° C. to about 50° C. Preferably the seeding is done at a temperature of at about 25° C. to about 35° C.

Step b) involves maintaining the reaction mixture of step a) at a temperature of about 0° C. to about 50° C.

The reaction mixture of step a) is maintained at a temperature of about of about 0° C. to about 50° C. for sufficient time. Sufficient time as disclosed herein is the time required to ensure the formation of crystalline nilotinib hydrochloride. In an embodiment, the reaction mixture is maintained for a time period of about 30 minutes to about 72 hours.

In an embodiment, the reaction mixture is maintained at a temperature of about 10° C. to about 40° C., more preferably at about 25° C. to about 35° C.

Step c) involves isolating nilotinib hydrochloride Form R5. The crystalline nilotinib hydrochloride Form R5 is isolated in a manner known per se, and depending on the solvent used, which include, but not limited to filtration by gravity or by suction/vacuum, distillation, centrifugation, or slow evaporation or the like. In an embodiment, nilotinib hydrochloride Form R5 may be isolated by filtration under vacuum, suction drying at a temperature of about 25° C. to about 35° C. and/or drying at a temperature of less than about 45° C.

Figure 2:
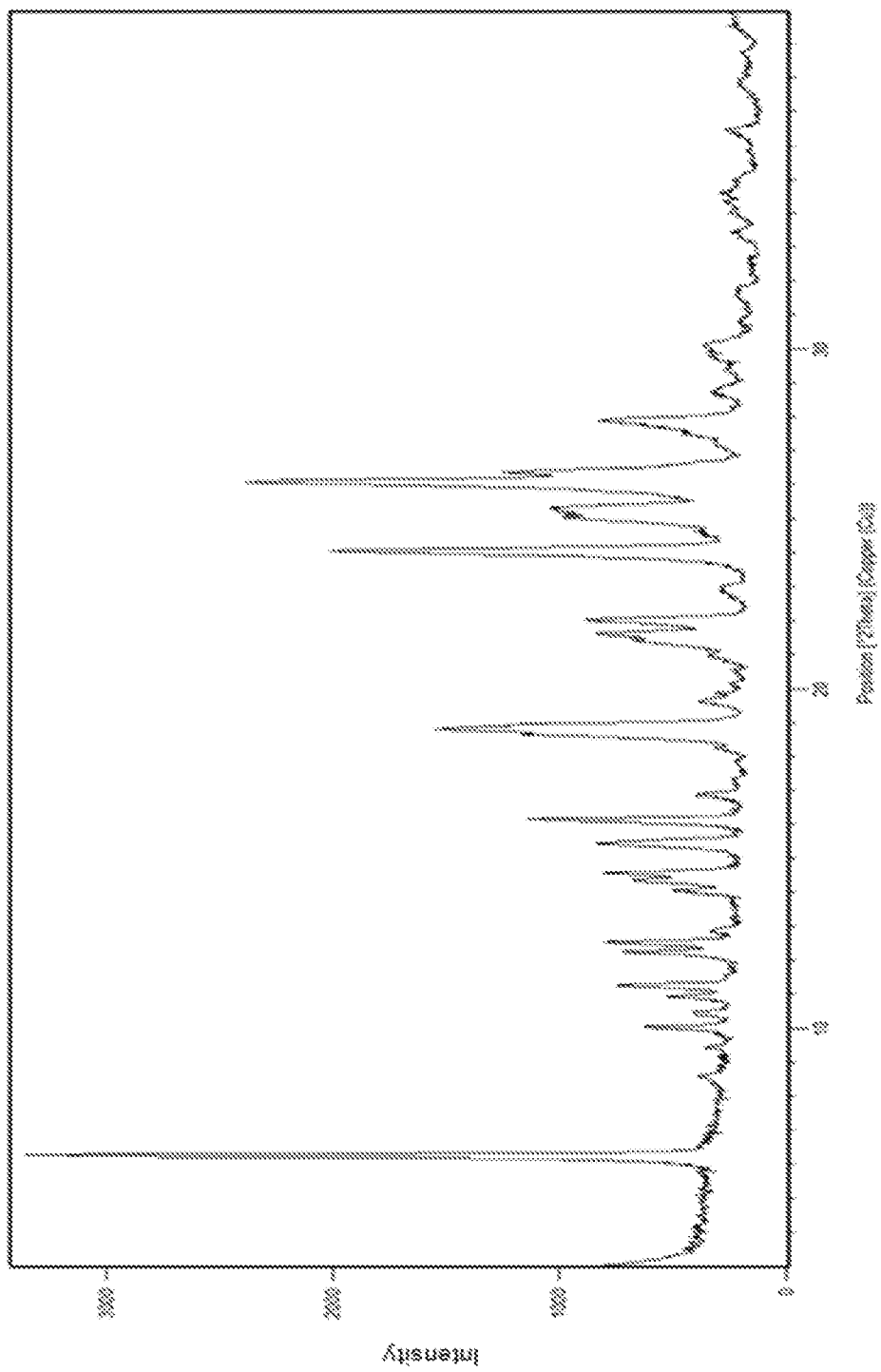

In an embodiment, the present application provides crystalline nilotinib hydrochloride, designated as Form R5a, characterized by data selected from the group consisting of: an x-ray powder diffraction pattern with peaks at about 6.29±0.2, 7.31±0.2, 15.45±0.2, 16.18±0.2, 24.10±0.2 and 26.15±0.2 degrees 2-theta; an x-ray powder diffraction pattern substantially as depicted in FIG. 2; and combinations thereof. Nilotinib hydrochloride Form R5a may be further characterized by an x-ray powder diffraction pattern having additional peaks at about 11.26±0.2, 12.25±0.2, 12.55±0.2, 18.86±0.2, 27.98±0.2 degrees 2-theta.

In another embodiment, the present application encompasses a process for preparing nilotinib hydrochloride Form R5a comprising, drying the crystalline nilotinib hydrochloride Form R5 at a temperature less than about 45° C.

Drying the crystalline nilotinib hydrochloride Form R5 may be suitably carried out using any equipment such as a gravity oven, tray dryer, vacuum oven, Büchi® Rotavapor®, air tray dryer, fluidized bed dryer, spin flash dryer, flash dryer, and the like. The drying may be carried out at atmospheric pressure or under reduced pressures, at temperatures less than about 45° C. In an embodiment, less than about 45° C. includes temperatures greater than 5° C. and less than 45° C. In an embodiment, the drying may be carried out at temperature of about 40° C., at a temperature of about 35° C., at a temperature of about 30° C., and any other suitable temperature. The drying may be carried out for any time periods required for obtaining a desired quality, such as from about 15 minutes to several hours, or longer.

In a specific embodiment, the present application encompasses a process for preparing nilotinib hydrochloride Form R5a comprising, drying the crystalline nilotinib hydrochloride Form R5 by using vacuum tray dryer or air tray dryer at a temperature less than about 45° C.

Figure 3:
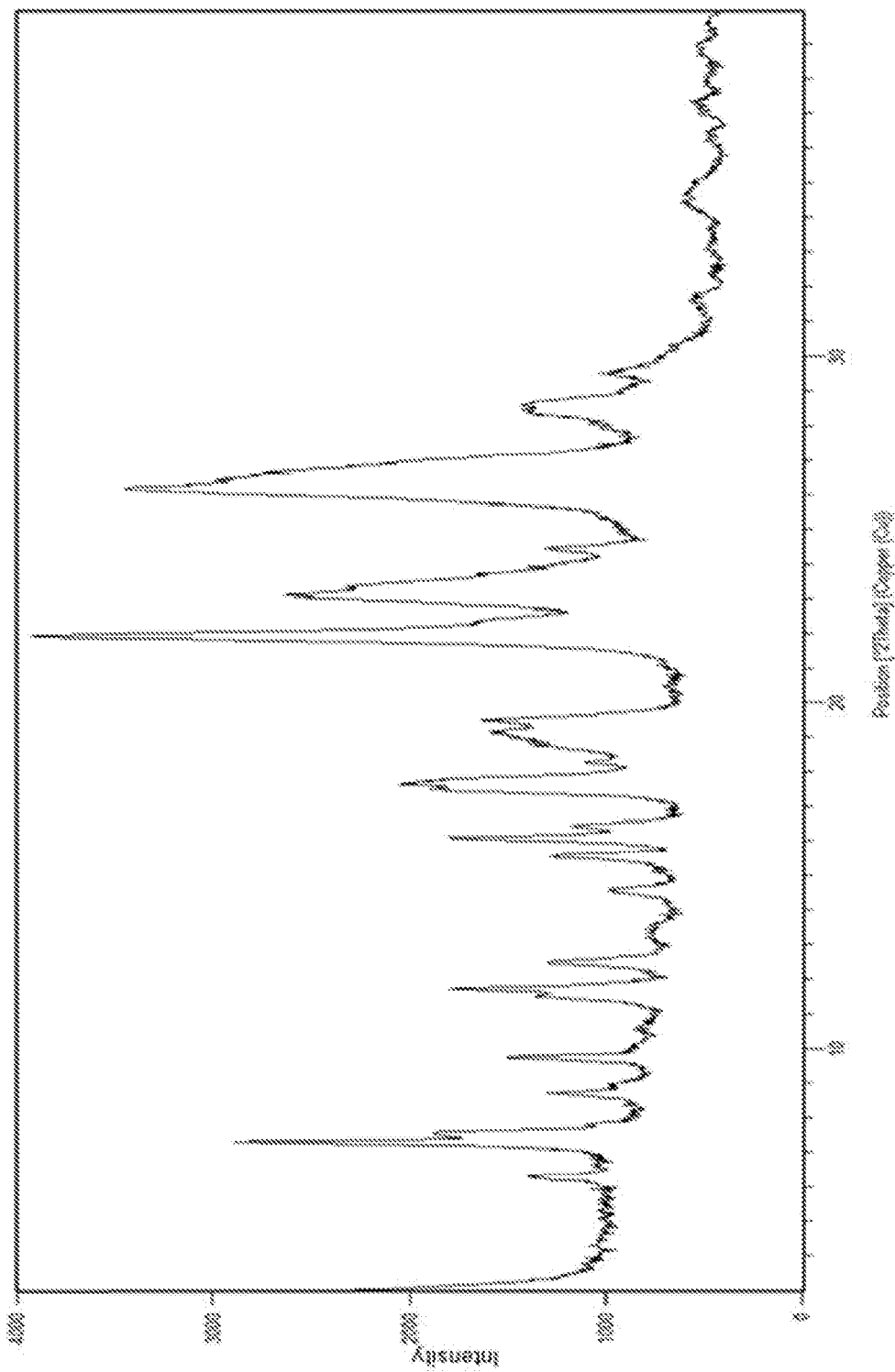
FIG. 3 illustrative a characteristic X-ray powder diffraction pattern of nilotinib hydrochloride Form R5b.

In an embodiment, the present application provides crystalline nilotinib hydrochloride, designated as Form R5b, characterized by data selected from the group consisting of: an x-ray powder diffraction pattern with peaks at about 6.28±0.2, 7.29±0.2, 7.56±0.2, 15.54±0.2, 16.07±0.2 and 21.91±0.2 degrees 2-theta; an x-ray powder diffraction pattern substantially as depicted in FIG. 3; and combinations thereof. Nilotinib hydrochloride Form R5b may be further characterized by an x-ray powder diffraction pattern having additional peaks at about 11.72±0.2, 12.45±0.2, 29.49±0.2 degrees 2-theta.

In another embodiment, the present application encompasses a process for preparing nilotinib hydrochloride Form R5b comprising, drying the crystalline nilotinib hydrochloride Form R5 or Form R5a at a temperature of about 60° C. to about 80° C.

Drying the crystalline nilotinib hydrochloride Form R5 or Form R5a may be suitably carried out using any equipment such as a gravity oven, tray dryer, vacuum oven, Büchi® Rotavapor®, air tray dryer, fluidized bed dryer, spin flash dryer, flash dryer, and the like. In an embodiment, the drying may be carried out at atmospheric pressure or under reduced pressures. In an embodiment, the drying may be carried out at a temperature of about 75° C., at a temperature of about 70° C., or at a temperature of about 65° C. The drying may be carried out for any time periods required for obtaining a desired quality, such as from about 15 minutes to several hours, or longer.

In a specific embodiment, the present application encompasses a process for preparing the nilotinib hydrochloride Form R5b comprising drying the crystalline nilotinib hydrochloride Form R5 or Form R5a in an air tray dryer or vacuum tray dryer at a temperature of about 60° C. to about 80° C. Preferably, the drying is carried out at a temperature of about 70° C.

Figure 4:
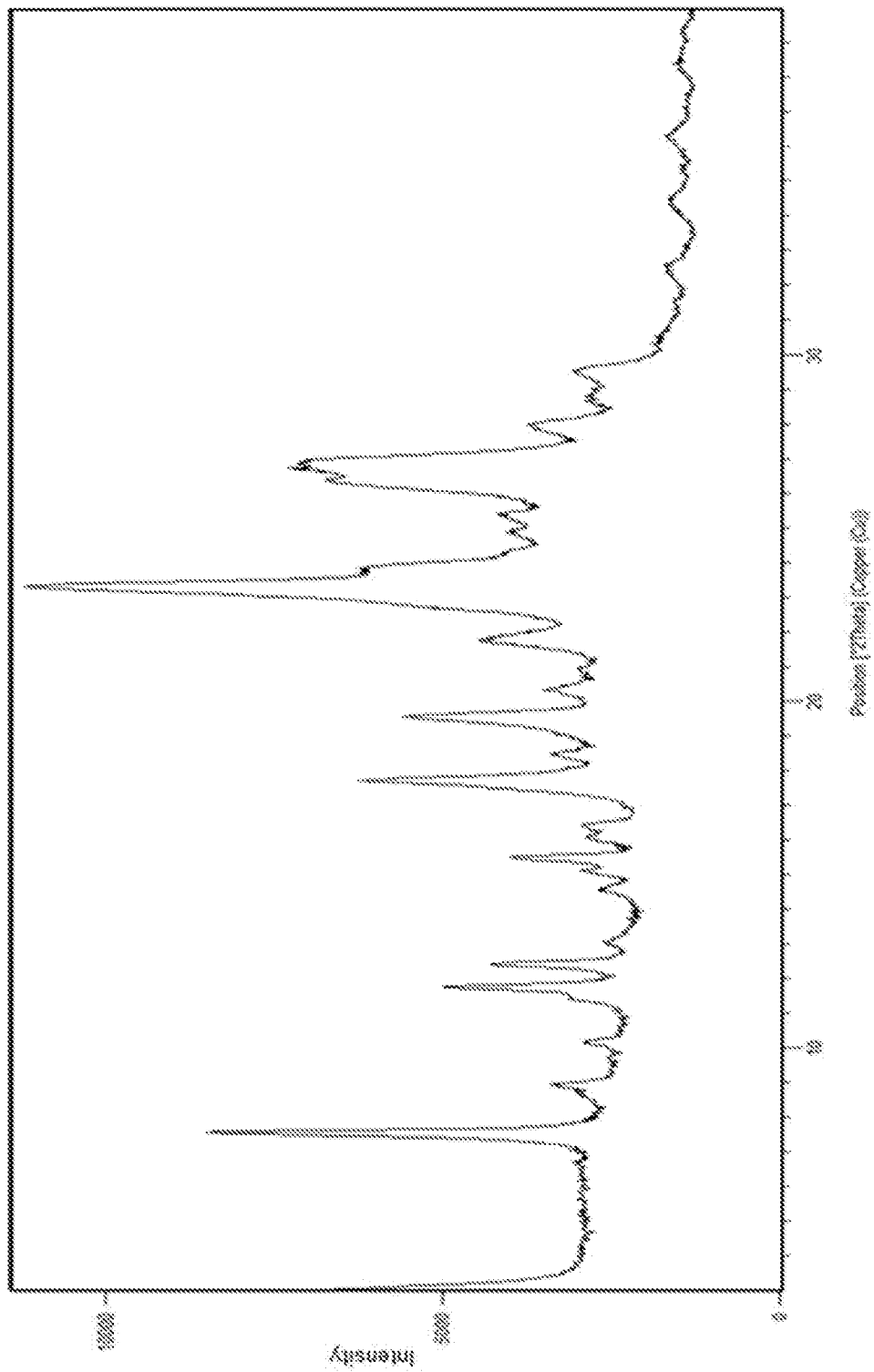
FIG. 4 illustrative a characteristic X-ray powder diffraction pattern of nilotinib hydrochloride Form R6.
Figure 5:
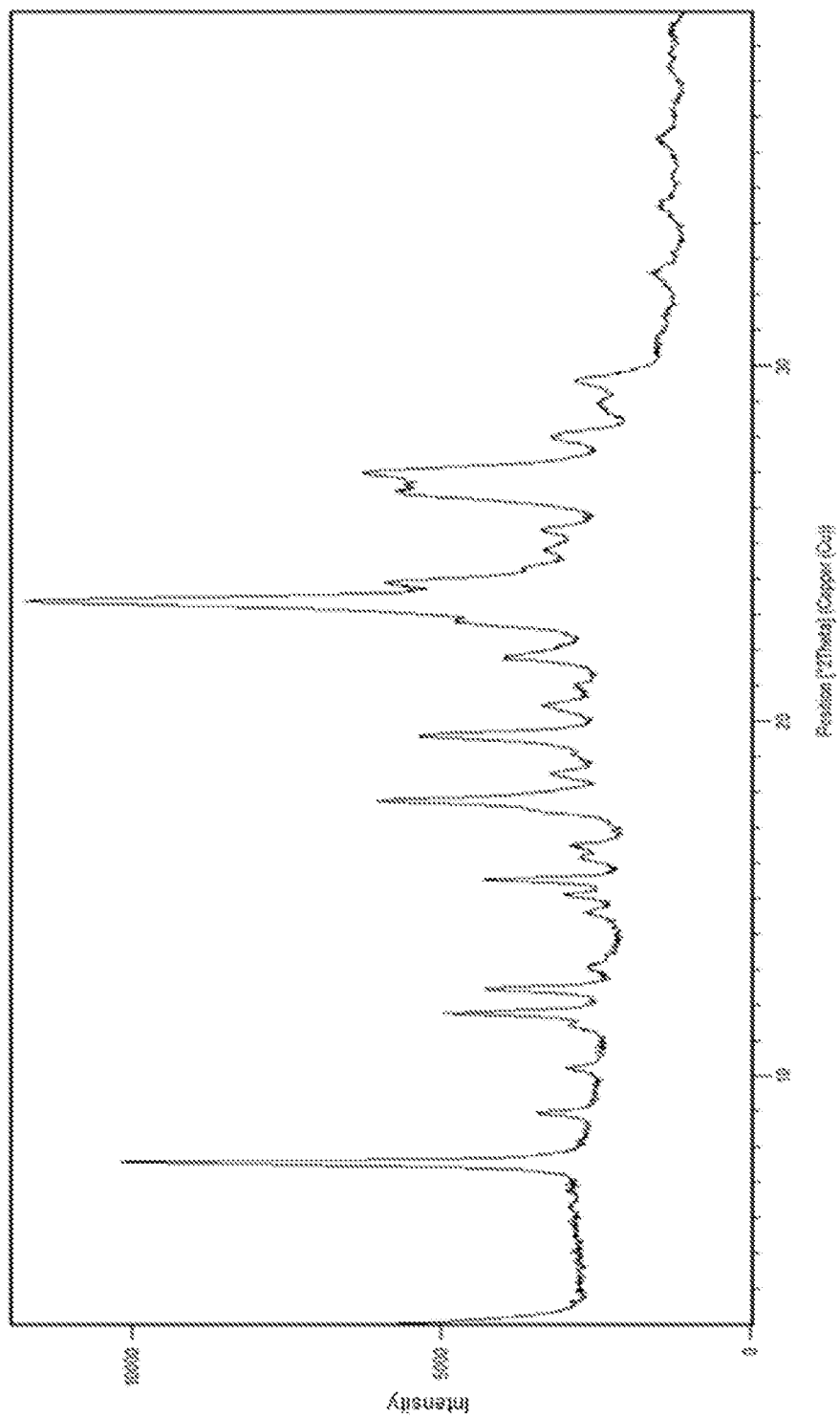
FIG. 5 illustrative a characteristic an X-ray powder diffraction pattern of nilotinib hydrochloride Form R6.

In an embodiment, the present application provides crystalline nilotinib hydrochloride, designated as Form R6, characterized by data selected from the group consisting of: an x-ray powder diffraction pattern with peaks at about 7.56±0.2, 10.16±0.2, 12.42±0.2, 20.32±0.2 and 27.97±0.2 degrees 2-theta; an x-ray powder diffraction pattern with peaks at about 8.93±0.2, 11.76±0.2, 15.53±0.2, 17.71±0.2, 19.57±0.2, 21.72±0.2 and 23.40±0.2 degrees 2-theta; an x-ray powder diffraction pattern substantially as depicted in FIG. 4; an x-ray powder diffraction pattern substantially as depicted in FIG. 5; and combinations thereof.

In another embodiment, the present application encompasses a process for preparing nilotinib hydrochloride Form R6 comprising the steps of:
 a) obtaining a solution of nilotinib hydrochloride in acetic acid;
 b) adding a hydrocarbon solvent and/or an ether solvent to the solution of step a);
 c) maintaining the reaction mixture of step b) at a temperature of about 0° C. to about 50° C.;
 d) isolating the obtained crystalline compound; and
 e) drying at a temperature of about 100° C. to about 120° C. to obtain nilotinib hydrochloride Form R6.

Step a) involves obtaining a solution of nilotinib hydrochloride in acetic acid.

Obtaining a solution according to step a) includes dissolving nilotinib hydrochloride in acetic acid or obtaining a solution of nilotinib hydrochloride in acetic acid as a final step in the preparation of the compound. Nilotinib hydrochloride may be obtained by the process known in the art. The solution of step a) may be provided at any temperature ranging from about 0° C. to about reflux temperature of the solvent, preferably at about 10° C. to about 80° C., more preferably at about 20° C. to about 50° C., most preferably at about 25° C. to about 35° C.

The solution may optionally be treated with activated charcoal and then filtered to remove the carbon. The solution may optionally be filtered by passing through paper, glass fiber, or other membrane material, or a bed of a clarifying agent such as Celite. Depending upon the equipment used, as well as the concentration and temperature of the solution, the filtration apparatus may need to be heated or cooled to avoid undesired crystallization.

Step b) involves adding a hydrocarbon solvent and/or an ether solvent to the solution of step a).

The hydrocarbon solvent that may be used in step b) is selected from n-pentane, n-heptane, n-hexane or the like. In a preferred embodiment, n-heptane is used. The ether solvent that may be used in step b) is selected from petroleum ether, diisopropyl ether, methyl tert-butyl ether or the like. In a preferred embodiment methyl tert-butyl ether is used.

In an embodiment, a hydrocarbon solvent and an ether solvent may be added to the solution of step a) in a sequential manner. For example, hydrocarbon solvent followed by an ether solvent or an ether solvent followed by a hydrocarbon solvent is added to the solution of step a).

In an embodiment, mixture of a hydrocarbon solvent and an ether solvent may be added to the solution of step a).

The hydrocarbon solvent and/or an ether solvent or mixtures thereof may be added to the solution obtained in step a) at a temperature of about 0° C. to about 50° C. Preferably at about 10° C. to about 40° C., more preferably at about 25° C. to about 35° C.

In a preferred embodiment, a hydrocarbon solvent followed by an ether solvent is added to the solution of step a) at a temperature of about 25° C. to about 35° C.

Optionally, seed crystals of Form R5 or R5a may be added to the reaction mixture of step b). The seed crystals of crystalline Form R5 may be obtained according to the process disclosed in the present application. The seed crystals of Form R5 may be added prior to the addition of a hydrocarbon or an ether solvent or after to the addition of a hydrocarbon or an ether solvent and before to step c). The seeding may be done at a temperature of about 0° C. to about 50° C. Preferably the seeding is done at a temperature of at about 25° C. to about 35° C. In an embodiment, the reaction mixture of step b) is obtained after the seeding step.

Step c) involves maintaining the reaction mixture of step b) at a temperature of about 0° C. to about 50° C.

The reaction mixture of step b) is maintained at a temperature of about of about 0° C. to about 50° C. for sufficient time. Sufficient time as disclosed herein is the time required to ensure the formation of crystalline nilotinib hydrochloride. In an embodiment, the reaction mixture is maintained for a time period of about 30 minutes to about 72 hours.

In an embodiment, the reaction mixture is maintained at a temperature of about 10° C. to about 40° C., more preferably at about 25° C. to about 35° C.

Step d) involves isolating nilotinib hydrochloride Form R5. The crystalline nilotinib hydrochloride Form R5 is isolated in a manner known per se, and depending on the solvent used, which include, but not limited to filtration by gravity or by suction/vacuum, distillation, centrifugation, or slow evaporation or the like. In an embodiment, nilotinib hydrochloride Form R5 may be isolated by filtration under vacuum, suction drying at a temperature of about 25° C. to about 35° C. and/or drying at a temperature of less than about 45° C.

Step e) involves drying the product at a temperature of about 100° C. to about 120° C. to obtain nilotinib hydrochloride Form R6.

Drying may be suitably carried out using any equipment such as a gravity oven, tray dryer, vacuum oven, Büchi® Rotavapor®, air tray dryer, fluidized bed dryer, spin flash dryer, flash dryer, and the like. In an embodiment, the drying may be carried out at atmospheric pressure or under reduced pressures. In an embodiment, the drying may be carried out at a temperature of about 120° C., at a temperature of about 115° C., at a temperature of about 110° C. or at a temperature of about 105° C. The drying may be carried out for any time periods required for obtaining a desired quality, such as from about 15 minutes to several hours, or longer.

In another embodiment, the present application encompasses a process for preparing nilotinib hydrochloride Form R6 comprising, drying the crystalline nilotinib hydrochloride Form R5 or Form R5a or Form R5b at a temperature of about 100° C. to about 120° C.

Drying the crystalline nilotinib hydrochloride Form R5 or Form R5a or Form R5b may be suitably carried out using any equipment such as a gravity oven, tray dryer, vacuum oven, Büchi® Rotavapor®, air tray dryer, fluidized bed dryer, spin flash dryer, flash dryer, and the like. In an embodiment, the drying may be carried out at atmospheric pressure or under reduced pressures. In an embodiment, the drying may be carried out at a temperature of about 120° C., at a temperature of about 115° C., at a temperature of about 110° C. or at a temperature of about 105° C. The drying may be carried out for any time periods required for obtaining a desired quality, such as from about 15 minutes to several hours, or longer.

In an embodiment, the present application encompasses a process for preparing nilotinib hydrochloride Form R6 comprising the steps of:

a) obtaining a suspension of nilotinib hydrochloride in acetic acid;
b) maintaining the suspension of step a) at a temperature of about 0° C. to about 50° C.; and
c) isolating the obtained crystalline compound; and
d) drying at a temperature of about 100° C. to about 120° C. to obtain nilotinib hydrochloride Form R6.

Step a) involves obtaining a suspension of nilotinib hydrochloride in acetic acid.

The nilotinib hydrochloride suspension according to step a) may be obtained by combining nilotinib hydrochloride with acetic acid at temperature of about 0° C. to about 50° C., preferably at about 10° C. to about 40° C., more preferably at about 25° C. to about 35° C. The amount acetic acid used for obtaining a suspension ranges from about 1 ml to about 5 ml per 1 g of nilotinib hydrochloride, based on the temperature range selected.

Step b) involves maintaining the suspension of step a) at a temperature of about 0° C. to about 50° C.

The suspension of step a) may be maintained at a temperature of about 0° C. to about 50° C. In an embodiment, the suspension of step a) is maintained at a temperature of about 10° C. to about 40° C., more preferably at about 25° C. to about 35° C. The suspension is maintained for a sufficient time to ensure the conversion of nilotinib hydrochloride to crystalline nilotinib hydrochloride Form R5. In an embodiment, the suspension is maintained for a time period of about 30 minutes to about 72 hours.

Step c) involves isolating the nilotinib hydrochloride Form R5. The crystalline nilotinib hydrochloride is isolated in a manner known per se, and depending on the solvent used, which include, but not limited to filtration by gravity or by suction/vacuum, distillation, centrifugation, or slow evaporation or the like. In an embodiment, nilotinib hydrochloride Form R5 may be isolated by filtration under vacuum, suction drying at a temperature of about 25° C. to about 35° C. and/or drying at a temperature of less than about 45° C.

Step d) involves drying the product of step c) at a temperature of about 100° C. to about 120° C. to obtain nilotinib hydrochloride Form R6.

Drying may be suitably carried out using any equipment such as a gravity oven, tray dryer, vacuum oven, Büchi® Rotavapor®, air tray dryer, fluidized bed dryer, spin flash dryer, flash dryer, and the like. In an embodiment, the drying may be carried out at atmospheric pressure or under reduced pressures. In an embodiment, the drying may be carried out at a temperature of about 120° C., at a temperature of about 115° C., at a temperature of about 110° C. or at a temperature of about 105° C. The drying may be carried out for any time periods required for obtaining a desired quality, such as from about 15 minutes to several hours, or longer.

In an embodiment, the present application encompasses a process for preparing nilotinib hydrochloride Form R6 comprising the steps of:
a) obtaining a slurry of nilotinib hydrochloride in acetic acid and ether solvent.
b) maintaining the slurry of step a) at a temperature of about 0° C. to about 50° C.;
c) isolating the obtained crystalline compound; and
d) drying at a temperature of about 100° C. to about 120° C. to obtain nilotinib hydrochloride Form R6.

Obtaining slurry according to step a) includes taking acetic acid and ether and adding nilotinib hydrochloride or dissolving nilotinib hydrochloride in acetic acid and adding ether. Nilotinib hydrochloride may be obtained by the process known in the art. The reaction mixture of step a) may be provided at any temperature ranging from about 0° C. to about reflux temperature of the solvent, preferably at about 10° C. to about 80° C., more preferably at about 20° C. to about 50° C., most preferably at about 25° C. to about 35° C.

The ether solvent that may be used in step a) is selected from petroleum ether, diisopropyl ether, methyl tert-butyl ether or the like. In a preferred embodiment methyl tert-butyl ether is used.

Optionally, seed crystals of Form R5 or R5a may be added to the reaction mixture of step a). The seed crystals of crystalline Form R5 may be obtained according to the process disclosed in the present application. The seeding may be done at a temperature of about 0° C. to about 50° C. Preferably the seeding is done at a temperature of at about 25° C. to about 35° C.

Step b) involves maintaining the reaction mixture of step a) at a temperature of about 0° C. to about 50° C.

The reaction mixture of step a) is maintained at a temperature of about of about 0° C. to about 50° C. for sufficient time. Sufficient time as disclosed herein is the time required to ensure the formation of crystalline nilotinib hydrochloride. In an embodiment, the reaction mixture is maintained for a time period of about 30 minutes to about 72 hours.

In an embodiment, the reaction mixture is maintained at a temperature of about 10° C. to about 40° C., more preferably at about 25° C. to about 35° C.

Step c) involves isolating nilotinib hydrochloride Form R5. The crystalline nilotinib hydrochloride Form R5 is isolated in a manner known per se, and depending on the solvent used, which include, but not limited to filtration by gravity or by suction/vacuum, distillation, centrifugation, or slow evaporation or the like. In an embodiment, nilotinib hydrochloride Form R5 may be isolated by filtration under vacuum, suction drying at a temperature of about 25° C. to about 35° C. and/or drying at a temperature of less than about 45° C.

Step d) involves drying the product at a temperature of about 100° C. to about 120° C. to obtain nilotinib hydrochloride Form R6.

Drying may be suitably carried out using any equipment such as a gravity oven, tray dryer, vacuum oven, Büchi® Rotavapor®, air tray dryer, fluidized bed dryer, spin flash dryer, flash dryer, and the like. In an embodiment, the drying may be carried out at atmospheric pressure or under reduced pressures. In an embodiment, the drying may be carried out at a temperature of about 120° C., at a temperature of about 115° C., at a temperature of about 110° C. or at a temperature of about 105° C. The drying may be carried out for any time periods required for obtaining a desired quality, such as from about 15 minutes to several hours, or longer.

In one embodiment, the present application provides pharmaceutical composition comprising crystalline form of nilotinib hydrochloride designated as Form R5, Form R5a, Form R5b, R6 and at least one pharmaceutically acceptable excipient.

Pharmaceutically acceptable excipients include, but are not limited to, suitable surface modifiers. Such excipients include various polymers, low molecular weight oligomers, natural products, and surfactants.

The crystalline forms of nilotinib hydrochloride designated as Form R5, Form R5a, Form R5b, and Form R6 of the present invention have advantageous properties selected from at least one: chemical purity, stability—such as storage stability, stability to dehydrate, stability to polymorphic conversion, flowability, solubility, morphology or crystal habit, low hygroscopicity and low content of residual solvents.

Certain specific aspects and embodiments of the present application will be explained in more detail with reference to the following examples, which are provided only for purposes of illustration and should not be construed as limiting the scope of the present application in any manner.

EXAMPLES

Example 1: Preparation of Nilotinib Hydrochloride Form R5

Nilotinib hydrochloride (1 g) and acetic acid (10 ml) were charged into a round bottom flask and stirred at 25-35° C. to obtain a solution. n-heptane (50 ml) was added and the mixture was stirred at 25-35° C. for 5 hours. Methyl tert-butyl ether (100 ml) was added and the mixture was stirred at the same temperature for about 18 hours. The obtained suspension was filtered and suction dried to obtain the title compound.

Example 2: Preparation of Nilotinib Hydrochloride Form R5

Nilotinib hydrochloride (5 g) and acetic acid (50 ml) were charged into a round bottom flask and stirred at 25-35° C. to obtain a solution. n-heptane (500 ml), methyl tert-butyl ether (100 ml) and seed material (0.5 g of Form R5) were added in sequence and the mixture was stirred at 25-35° C. Methyl tert-butyl ether (400 ml) was added and the mixture was stirred at the same temperature for about 48 hours. The obtained suspension was filtered and suction dried to obtain the title compound.

Example 3: Preparation of Nilotinib Hydrochloride Form R5

Nilotinib hydrochloride (3 g) and acetic acid (5 ml) were charged into a round bottom flask at 25-35° C. to obtain a suspension. The mixture was stirred at the same temperature for about 20 hours, filtered and suction dried to obtain the title compound.

Example 4: Preparation of Nilotinib Hydrochloride Form R5a

Nilotinib hydrochloride Form R5 (500 mg) was dried in an air tray dryer for 1 hour at a temperature of 40° C. to provide the title compound.

Example 5: Preparation of Nilotinib Hydrochloride Form R5a

Nilotinib hydrochloride Form R5 (500 mg) was dried in a vacuum tray dryer for 1 hour at a temperature of 40° C. to provide the title compound.

Example 6: Preparation of Nilotinib Hydrochloride Form R5b

Nilotinib hydrochloride Form R5a (500 mg) was dried in an air tray dryer for about 8 hours at a temperature of 70° C. to provide the title compound.

Example 7: Preparation of Nilotinib Hydrochloride Form R6

Nilotinib hydrochloride (5 g) and acetic acid (50 ml) were charged into a round bottom flask and stirred at 25-35° C. to obtain a solution. n-heptane (500 ml), methyl tert-butyl ether (100 ml) and seed material (0.5 g of Form R5) were added in sequence and the mixture was stirred at 25-35° C. Methyl tert-butyl ether (400 ml) was added and the mixture was maintained at the same temperature for about 48 hours. The obtained suspension was filtered, suction dried, dried in a vacuum tray dryer for 1 hour at a temperature of 40° C. and further dried in a vaccum tray dryer for 8 hours at a temperature of 100° C. to obtain Nilotinib hydrochloride Form R6. Yield: 89%

Example 8: Preparation of Nilotinib Hydrochloride Form R6

Nilotinib hydrochloride (5 g) and acetic acid (50 ml) were charged into a round bottom flask and stirred at 25-35° C. to obtain a solution. n-heptane (500 ml), methyl tert-butyl ether (100 ml) and seed material (0.5 g of Form R5) were added in sequence and the mixture was stirred at 25-35° C. Methyl tert-butyl ether (400 ml) was added and the mixture was maintained at the same temperature for about 48 hours. The obtained suspension was filtered, suction dried, dried in a vacuum tray dryer for 1 hour at a temperature of 40° C. and further dried in a vacuum tray dryer for 14 hours at a temperature of 100° C. to obtain Nilotinib hydrochloride Form R6.
Yield: 89.3%; PXRD: FIG. 4.

Example 9: Preparation of Nilotinib Hydrochloride Form R6

Nilotinib hydrochloride (3 g) and acetic acid (5 ml) were charged into a round bottom flask at 25-35° C. to obtain a suspension. The mixture was stirred at the same temperature for about 20 hours, filtered and suction dried. The obtained compound was dried in a dried in an air tray dryer for 1 hour at a temperature of 40° C. and further dried in an air tray dryer for 4 hours at a temperature of 100° C. to obtain Nilotinib hydrochloride Form R6.
Yield: 57.48%; PXRD: FIG. 5.

Example 10: Preparation of Nilotinib Hydrochloride Form R6

15.0 mL of methyl tert-butyl ether and 5.0 mL of acetic acid were charged into a round bottom flask at 26° C. 1.0 g of nilotinib hydrochloride was charged to the round bottom flask and stirred for 23 hours at 26° C. The material was filtered using a suction pump and dried for 5 minutes. The obtained material was dried on air tray dryer at 110° C. for 6 hours to obtain the titled compound.
Yield: 95%

Example 11: Preparation of Nilotinib Hydrochloride Form R6

15.0 g of nilotinib hydrochloride and 75 mL of acetic acid were charged into a round bottom flask at 30° C. and stirred for 15 minutes. 75.0 mL of n-heptane and 30.0 mL of methyl tert-butyl ether were added to the above flask. The above flask was seeded with 0.75 g of R5 material (as prepared in any of the above example) and stirred for 5 minutes. 270 mL of methyl tert-butyl ether was added over a 5 minutes period and the contents were stirred for 15 hours at 30° C. The material was filtered using a suction pump and washed with 30 mL methyl tert-butyl ether. The material was sifted through 25 mesh sieve and dried in air tray dryer at 110° C. for 6 hours to obtain the titled compound.

Yield: 73%

Example 12: Preparation of Nilotinib Hydrochloride Form R6

375 mL of methyl tert-butyl ether and 125 mL of acetic acid were charged into a round bottom flask at 27° C. 25.0 g of nilotinib hydrochloride was charged in the above flask and maintained under stirring for 24 hours at 27° C. The material was filtered using a suction pump at 27° C. The material was sifted through 25 mesh sieve and dried in air tray dryer at 110° C. for 6 hours to obtain the title compound.

Yield: 19.5 g

We claim:

1. Crystalline Form R5 of nilotinib hydrochloride characterized by powder X-ray diffraction pattern (PXRD) with peaks at about 6.27±0.2, 15.44±0.2, 16.15±0.2, 24.07±0.2 and 26.11±0.2 degrees 2-theta.

2. Crystalline Form R5 of nilotinib hydrochloride of claim 1, further characterized by powder X-ray diffraction pattern (PXRD) with peaks at about 11.26±0.2, 12.24±0.2, 12.54±0.20, 18.81±0.2 and 27.94±0.2 degrees 2-theta.

3. Crystalline Form R5 of nilotinib hydrochloride characterized by a PXRD pattern substantially as depicted in FIG. 1.

4. A process for preparing nilotinib hydrochloride Form R5 of claim 1 comprising the steps of:
 a) obtaining a solution of nilotinib hydrochloride in acetic acid;
 b) adding a hydrocarbon solvent and/or an ether solvent to the solution of step a);
 c) maintaining at a temperature of about 0° C. to about 50° C.; and
 d) isolating nilotinib hydrochloride Form R5.

5. The process of claim 4, wherein a hydrocarbon solvent is n-heptane.

6. The process of claim 4, wherein an ether solvent is methyl tert-butyl ether.

7. A process for preparing nilotinib hydrochloride Form R5 of claim 1 comprising the steps of:
 a) obtaining a suspension of nilotinib hydrochloride in acetic acid;
 b) maintaining the suspension of step a) at a temperature of about 0° C. to about 50° C.; and
 c) isolating nilotinib hydrochloride Form R5.

8. A process for preparing nilotinib hydrochloride Form R5 of claim 1 comprising the steps of:
 a) obtaining slurry of nilotinib hydrochloride in acetic acid and ether solvent;
 b) maintaining the slurry of step a) at a temperature of about 0° C. to about 50° C.;
 c) isolating nilotinib hydrochloride Form R5.

9. The process of claim 8, wherein the ether solvent is methyl tert-butyl ether.

* * * * *